United States Patent
Gilboa (10) Patent No.: US 8,565,858 B2
(45) Date of Patent: Oct. 22, 2013

(54) METHODS AND SYSTEMS FOR PERFORMING MEDICAL PROCEDURES WITH REFERENCE TO DETERMINING ESTIMATED DISPOSITIONS FOR ACTUAL DISPOSITIONS OF PROJECTIVE IMAGES TO TRANSFORM PROJECTIVE IMAGES INTO AN IMAGE VOLUME

(75) Inventor: Pinhas Gilboa, Haifa (IL)

(73) Assignee: Covidien LP, Mansfield, MA (US)

( * ) Notice: Subject to any disclaimer, the term of this patent is extended or adjusted under 35 U.S.C. 154(b) by 278 days.

(21) Appl. No.: 12/490,237

(22) Filed: Jun. 23, 2009

(65) Prior Publication Data

US 2009/0264729 A1   Oct. 22, 2009

Related U.S. Application Data (62) Division of application No. 10/169,186, filed as application No. PCT/US01/00074 on Jan. 2, 2001, now abandoned.

(60) Provisional application No. 60/175,226, filed on Jan. 10, 2000.

(51) Int. Cl.
 *G03B 42/02* (2006.01)
 *G01T 1/00* (2006.01)

(52) U.S. Cl.
 USPC .......................................... 600/425; 378/21

(58) Field of Classification Search
 None
 See application file for complete search history.

(56) References Cited

U.S. PATENT DOCUMENTS

| | | |
|---|---|---|
| 4,686,695 A | 8/1987 | Macovski |
| 5,042,486 A | 8/1991 | Pfeiler et al. |
| 5,251,635 A | 10/1993 | Dumoulin et al. |
| 5,376,795 A * | 12/1994 | Hasegawa et al. ....... 250/363.04 |
| 5,383,454 A | 1/1995 | Bucholz |
| 5,588,033 A | 12/1996 | Yeung |
| 5,622,170 A | 4/1997 | Schulz |
| 5,638,819 A | 6/1997 | Manwaring et al. |
| 5,647,361 A | 7/1997 | Damadian |
| 5,744,802 A * | 4/1998 | Muehllehner et al. ... 250/363.03 |

(Continued)

FOREIGN PATENT DOCUMENTS

| | | |
|---|---|---|
| WO | 99/26826 A2 | 6/1999 |
| WO | 00/16684 A1 | 3/2000 |
| WO | 0010456 A1 | 3/2000 |

OTHER PUBLICATIONS

G. Ramm and A.I. Katsevich, The Radon Transform and Local Tomography, CRC Press, 1996.

(Continued)

*Primary Examiner* — Jacqueline Cheng
(74) *Attorney, Agent, or Firm* — Carter DeLuca Farrell & Schmidt LLP (57) ABSTRACT

A catheter is navigated within a body cavity of a patient. This navigation is enabled by the provision of the transmitter of electromagnetic radiation under platform, a receiver of electromagnetic radiation rigidly attached to fluoroscope, and a receiver of radiation rigidly attached to the catheter, all three of which are connected by wires to a computer. The computer displays, on a display unit, the image of the body cavity acquired by the fluoroscope, with an icon representing the catheter superposed on the image in the location and orientation of catheter relative to the body. There is no representational imaging device equipped with a receiver in the apparatus of the current invention.

7 Claims, 7 Drawing Sheets

(56) References Cited

U.S. PATENT DOCUMENTS

| | | | |
|---|---|---|---|
| 5,772,594 A | 6/1998 | Barrick | |
| 5,829,444 A | 11/1998 | Ferre et al. | |
| 5,873,822 A | 2/1999 | Ferre et al. | |
| 5,902,239 A | 5/1999 | Buurman | |
| 5,909,476 A * | 6/1999 | Cheng et al. | 378/4 |
| 5,980,504 A | 11/1999 | Sharkey et al. | |
| 6,092,928 A * | 7/2000 | Mattson et al. | 378/205 |
| 6,139,183 A | 10/2000 | Graumann | |
| 6,149,592 A | 11/2000 | Yanof et al. | |
| 6,307,908 B1 * | 10/2001 | Hu | 378/4 |
| 6,314,310 B1 | 11/2001 | Ben-Haim et al. | |
| 6,470,207 B1 | 10/2002 | Simon et al. | |
| 6,484,049 B1 * | 11/2002 | Seeley et al. | 600/426 |
| 6,580,938 B1 | 6/2003 | Acker | |
| 7,016,457 B1 * | 3/2006 | Senzig et al. | 378/19 |
| 2002/0045916 A1 | 4/2002 | Gray et al. | |

OTHER PUBLICATIONS

F. Natterer, The Mathematics of Computerized Tomography, Wiley, 1989.

G.T. Herman et al., Basic Methods of Tomography and Inverse Problems, Hildger, 1987.

G.T. Herman and Attila Kuba, Discrete Tomography, Birhauser, 1999.

\* cited by examiner

METHODS AND SYSTEMS FOR PERFORMING MEDICAL PROCEDURES WITH REFERENCE TO DETERMINING ESTIMATED DISPOSITIONS FOR ACTUAL DISPOSITIONS OF PROJECTIVE IMAGES TO TRANSFORM PROJECTIVE IMAGES INTO AN IMAGE VOLUME

RELATED APPLICATIONS

This application is a divisional of and claims priority to U.S. patent application Ser. No. 10/169,186 filed Jun. 28, 2002 now abandoned entitled Methods And Systems For Performing Medical Procedures With Reference To Projective Image And With Respect To Pre-Stored Images, which claims priority to International Patent Application No. PCT/US01/00074, International Filing Date Jan. 2, 2001, entitled Methods And Systems For Performing Medical Procedures With Reference To Projective Images And With Respect To Pre-Stored Images, which claims benefit of U.S. Provisional Application Ser. No. 60/175,226 filed Jan. 10, 2000 entitled Interventional 3D Fluoroscope, all of which are hereby incorporated herein by reference.

FIELD AND BACKGROUND OF THE INVENTION

The present invention relates to medical procedures that are performed with reference to images of the patient and, more particularly, to medical procedures performed with reference to projective images such as fluoroscope images, and also to medical procedures performed with reference to images acquired prior to, and independently of, the procedures.

Images of the interiors of patients commonly are used to guide the performance of invasive medical procedures on the patients. Bucholtz, in U.S. Pat. No. 5,383,454, Ferre et al., in U.S. Pat. Nos. 5,829,444 and 5,873,822, and Bourman, in U.S. Pat. No. 5,902,239, teach the navigation of a probe, such as a catheter, within the body of a patient, with reference to previously acquired images. Barrick, in U.S. Pat. No. 5,772,594, teaches fluoroscopic imaging of a bone prior to the insertion therein of a guide pin or screw with reference to the image.

Two kinds of imaging modalities are in common use. Representational images, such as CT images, MR images and ultrasound images, represent physical properties of the patient's body at particular locations therein. For example, each pixel of a 2D digital ultrasound image of a patient represents an acoustic impedance contrast at a corresponding point inside the patient's body, and each voxel of a 3D CT image volume represents the density of the patient's body tissue at a corresponding point inside the patient's body. Projective images, such as fluoroscopic X-ray images, represent projections of physical properties of the patient's body into a plane. For example, each point in a fluoroscopic X-ray image is an integral along a ray, from the X-ray source to the X-ray image, of the density of the patient's body tissue.

Figure 1A:
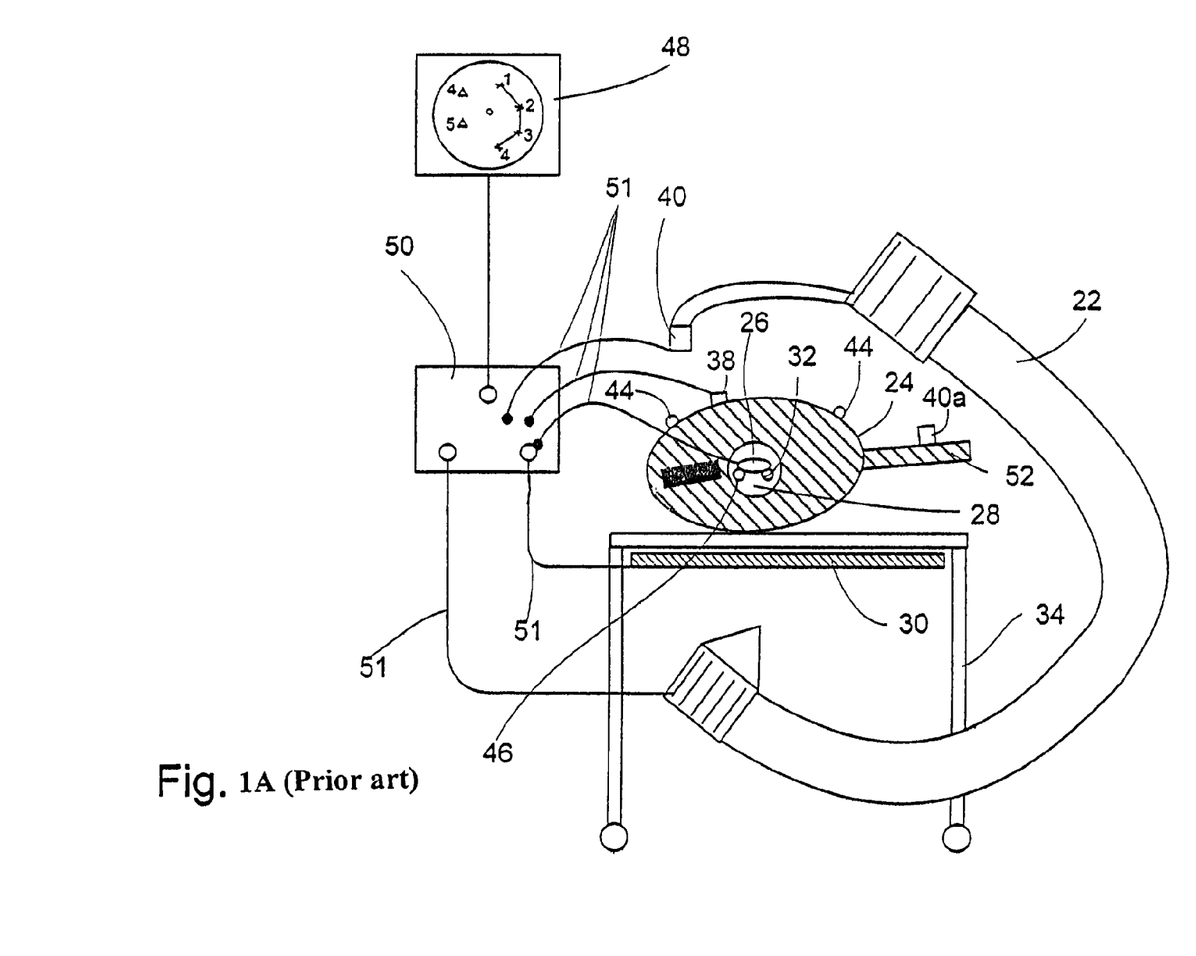
FIG. 1A (prior art) illustrates a system for intra-body navigation of a probe towards a point-of-interest in a body cavity of a patient, with the help of a protective imaging device and a representational imaging device.

Two prior art references of particular note are Gilboa et al., WO 00/10456 and WO 00/16684, both of which documents are incorporated by reference for all purposes as if fully set forth herein. WO 00/10456 teaches intra-body navigation of a probe in conjunction with imaging by a C-mount fluoroscope. WO 00/16684 teaches the use of a representational imaging device, such as an ultrasound probe, in conjunction with the C-mount fluoroscope of WO 00/10456, for the purpose of identifying and recording points-of-interest, within the body of the patient, towards which the probe subsequently is navigated. FIG. 1A, which is adapted from FIG. 2 of WO 00/16684, shows a patient 24 lying on an operation platform 34 and being imaged by a C-mount fluoroscope 22. A catheter 26 is navigated within a body cavity 28 of patient 24. This navigation is enabled by the provision of a transmitter 30 of electromagnetic radiation under-platform 34, a receiver 40 of electromagnetic radiation rigidly attached to fluoroscope 22, and a receiver 32 of radiation rigidly attached to catheter 26, all three of which are connected by wires 51 to a computer 50. Fluoroscope 22 is used to acquire an image of a portion of the body of patient 24 that includes body cavity 28. As explained in WO 00/10456, transmitter 30 defines a reference frame, and the signals received by computer 50 from receivers 40 and 32 in response to the electromagnetic radiation transmitted by transmitter 30 are indicative of the locations and orientations of fluoroscope 22 and catheter 26 relative to the reference frame. Given these locations and orientations, computer 50 displays, on a display unit 48, the image of body cavity 28 acquired by fluoroscope 22, with an icon representing catheter 26 superposed on the image in the true location and orientation of catheter 26 relative to body cavity 28.

Because patient 24 may move, relative to platform 34, during the medical procedure, patient 24 also is provided with a receiver 38 of electromagnetic radiation. Computer 50 computes, from the signals received from receiver 38 in response to the electromagnetic radiation transmitted by transmitter 30, the location and orientation of the body of patient 24 relative to the reference frame. This is in addition to the computation, by computer 50, from the signals received from receiver 40, of the location and orientation of fluoroscope 22 relative to the reference frame, and in addition to the computation, by computer 50, from the signals received from receiver 32, of the location and orientation of catheter 26 relative to the reference frame. Computer 50 records the location and orientation of patient 24 when the image of body cavity 28 is acquired. If patient 24 does moves, computer 50 adjusts the joint display of the image and the catheter icon on display unit 48 to reflect the movement of patient 24, so that the catheter icon always is displayed in a manner that reflects the true location and orientation of catheter 26 relative to body cavity 28.

As alternatives to receivers 32 and 44, catheter 26 and patient 24 are provided with respective imagable markers 46 and 44. Computer 50 locates the shadows of markers 46 and 44 in the image, using standard image processing techniques, and computes, from the locations of these shadows, the locations and orientations of catheter 26 and patient 24.

A representational imaging device 52, equipped with a receiver 40a of electromagnetic radiation, also is provided, to acquire a representational image of a portion of the body of patient 24 that overlaps with the portion of the body of patient 24 that is acquired using fluoroscope 22. Computer 50 computes, from the signals received from receiver 40a in response to the electromagnetic radiation transmitted by transmitter 30, the location and orientation of imaging device 52 relative to the reference frame. Computer 50 then displays the representational image, on display unit 48, superposed on the image acquired by fluoroscope 22, so that a point-of-interest, towards which catheter 26 is to be navigated, can be picked on display unit 48, even prior to the introduction of catheter 26 into body cavity 28. Improved methods of effecting this superposition are taught by Gilboa et al. in PCT application US99/26826, which also is incorporated by reference for all purposes as if fully set forth herein. Because computer 50 tracks the movement of both patient 24 and catheter 26, an icon representing the point-of-interest is displayed on display unit 48 in a manner that represents the true location of the point-of-interest in body cavity 28, so that catheter 26 can be navigated Jo the point-of-interest with reference to the relative locations, as displayed by display unit 48, of the icon representing catheter 26 and of the icon representing the point-of-interest.

Representational imaging device 52 may be external to the body of patient 24, as illustrated in FIG. 1A, or internal to the body of patient 24. The specific example of representational imaging device 52 that is presented in WO 00/16684 is an intracardiac ultrasound probe that is used to image and identify the fossa ovalis of the cardiac septum and one or more of the openings of pulmonary veins. These points within the heart may be targets of ablation for treating atrial fibrillation, and so constitute points-of-interest within the heart (as body cavity 28) of patient 24. Following the representational imaging of these targets by intracardiac ultrasound probe 52 and the picking of the points-of-interest, intracardiac ultrasound probe 52 is withdrawn and an ablating catheter 26 is navigated towards the points-of-interest.

Transmitter 30 is an example of what is called in WO 00/16684 a "locating implement". Receivers 32, 38, 40 and 40a are examples of what is called in WO 00/16684 "location implements". Transmitter 30, together with receiver 32, 38, 40 or 40a constitute what is called in WO 00/16684 a "locating system". In the present context, the location and the orientation of an object are called the "disposition" of the object, so what WO 00/16684 calls a "locating system" is called herein a "disposing system". Similarly, what WO 00/16684 calls a "locating implement" is called herein a "disposing implement", and what WO 00/16684 calls a "location implement" is called herein a "disposition implement". The term "location system" is used herein to refer, not only to systems that measure both the location and the orientation of an object, but also to systems that measure only the location of an object; such a system includes a locating implement and a location implement. Note that when multiple disposing systems are used, one disposing instrument may be shared by all the disposing systems as is the case with transmitter 30, in which case the shared disposing instrument defines a common reference frame for all the disposing systems; or, alternatively, one disposition implement may be shared by all the disposing systems, in which case the shared disposition instrument defines a common reference frame for all the disposing systems. Common examples of disposing systems include electromagnetic disposing systems, magnetic disposing systems, acoustic disposing systems and stereopair optical systems.

One invasive medical procedure for which the prior art methods are not quite suitable is the deployment of a stent in a partially blocked coronary artery. This procedure commonly is performed by injecting a contrast agent into the target coronary artery tree and then navigating a catheter that bears the stent towards the target blockage with the help of X-ray angiographic images acquired in real time by a fluoroscope such as fluoroscope 22. In this case, the points-of-interest are the blockage itself, and the branches of the coronary artery tree that must be traversed on the way to the blockage. In principle, the prior art discussed above can be used to identify the points-of-interest, provided that these points-of-interest can be picked on the image provided by representational imaging device 52. For example, representational imaging device 52 may be a CT scanner: the contrast agent, being X-ray opaque, shows up in both the projective images acquired using fluoroscope 22 and the representational CT scan acquired using the CT scanner. This has the disadvantage of requiring the use of two imaging modalities, one of which (CT) is not suitable for real-time imaging. Furthermore, it is relatively difficult to register a CT image volume with a fluoroscopic image.

There is thus a widely recognized need for, and it would be highly advantageous to have, a method, of navigating a probe to a point-of-interest in a body cavity of a patient, that is based on a single projective imaging modality.

A CT scanner produces its representational image volume by appropriate processing (typically, by backprojection) of a set of projective images. In principle, then, it should be possible to use fluoroscope 22 itself as both a projective imager and a representational imager. Yeung, in U.S. Pat. No. 5,588,033, which is incorporated by reference for all purposes as if fully set forth herein, teaches the reconstruction of a binary (two-level) image volume from a relatively small set of projective radiographic images. In principle, a similar reconstruction should be possible using fluoroscopic images acquired at different dispositions relative to patient 24. In particular, in the stent deployment discussed above, a binary representational image volume of the contrast agent in the coronary artery tree would show the portion of the coronary artery tree that contains the contrast agent at one of the two display levels (e.g., "1") and the rest of the imaged portion of the patient's body at the other level (e.g., "0"), and so would suffice to allow picking of the points-of-interest. In practice, however, fluoroscope 22 lacks sufficient mechanical stability to allow accurate reconstruction of even a binary image volume. Known successful reconstructions of image volumes from 2D projective images all require very accurate positioning of the imaging apparatus. Conventional CT scanners include heavy and very accurate mechanisms for rotating their X-ray sources and detectors and similarly heavy and accurate sliding mechanisms for moving the platform on which the patient lies. Yeung uses a stereotactic localizer frame to provide the required dispositional accuracy.

There is thus a widely recognized need for, and it would be highly advantageous to have, a method of transforming a set of projective images, acquired using a projective imager of limited mechanical stability, into a representational image volume.

Returning to the procedure for deploying a stent in a coronary artery, the fluoroscope commonly is placed in a disposition relative to the patient that is expected to give the best projective view of the target coronary artery tree. The contrast agent is injected into the coronary tree, and the projective image is acquired and digitized. This projective image is used as a background "road map" for catheter navigation with the help of other images subsequently acquired of the target coronary artery tree, but only if the fluoroscope and the patient remain in the same relative disposition. Movement of either the fluoroscope or the patient renders this projective image useless as a road map. In particular, if the disposition of the fluoroscope relative to the patient turns out to be suboptimal, or if the patient must be imaged from several dispositions of the fluoroscope in order to give an adequate picture of the three-dimensional structure of the coronary artery tree, then for each new disposition of the fluoroscope, the contrast agent must be injected anew and a new road map must be acquired. This exposes both the medical team and the patient to additional X-radiation, and also exposes the patient to the danger of liver damage from repeated injections of the contrast agent.

There is thus a widely recognized need for, and it would be highly advantageous to have, a method of acquiring and using X-ray angiographic road maps without undue danger to either the patient or the medical team.

SUMMARY OF THE INVENTION

According to the present invention there is provided a method of navigating a probe to a target point-of-interest in a body cavity of a patient, including the steps of: (a) acquiring a plurality of projective images of at least a portion of the body cavity, using a projective imaging device, each projective image being acquired with the projective imaging device in a different respective disposition relative to a reference frame; (b) for each projective image, measuring the respective disposition of the projective imaging device; (c) estimating a location of the target point-of-interest, relative to the reference frame, from the protective images, the estimating being based on the measured dispositions of the projective imaging device; (d) inserting the probe into the body cavity; (e) measuring a location of the probe relative to the reference frame; and (f) moving the probe, within the body cavity, so as to minimize a difference between the measured location of the probe and the estimated location of the target point-of-interest.

According to the present invention there is provided a navigating system for navigating a probe to a point-of-interest in a body, cavity of a patient, including: (a) a projective imaging device for acquiring a plurality of projective images of at least a portion of the body cavity; (b) a disposing system for measuring, for each projective image, a respective disposition of the projective imaging device relative to a reference frame; (c) a mechanism for estimating a location of the point-of-interest, relative to the reference frame, from the projective images, the estimating being based on the measured dispositions of the projective imaging device; and (d) a locating system for measuring a location of the probe relative to the reference frame.

According to the present invention there is provided a method of acquiring an image volume of a body, including the steps of: (a) for each of a plurality of nominal dispositions of a projective imaging device relative to a reference frame: (i) measuring an actual disposition of the projective imaging device relative to the reference frame, (ii) if the actual disposition is not substantially the same as the each nominal disposition, moving the projective device until the actual disposition is substantially the same as the each nominal disposition, and (iii) acquiring a respective projective image of the body, using the projective imaging device at the each nominal disposition; and (b) transforming the plurality of projective images into the image volume.

According to the present invention there is provided an imaging system for acquiring an image volume of a body, including: (a) a projective imaging device for acquiring projective images of the body; (b) a disposing system for measuring dispositions of the projective imaging device relative to a reference frame; (c) a mechanism for moving the projective imaging device among a plurality of nominal dispositions thereof, with reference to the measured disposition; and (d) a processor for transforming the projective images into the image volume, each projective image having been acquired at a different respective nominal disposition.

According to the present invention there is provided a method of acquiring an image volume of a body, including the steps of: (a) for each of a plurality of dispositions of a projective imaging device relative to a reference frame: (i) moving the imaging device to the disposition, as measured by a disposing system, and (ii) acquiring a respective projective image of the body; and (b) transforming the projective images into the image volume according to the measurements of the dispositions.

According to the present invention there is provided an imaging system for acquiring an image volume of a body, including: (a) a projective imaging device for acquiring projective images of the body; (b) a disposing system for measuring dispositions of the projective imaging device relative to a reference frame; and (c) a processor for transforming the projective images into the image volume according to the measured dispositions.

According to the present invention there is provided a method of acquiring an output image volume of a body, including the steps of: (a) for each of a plurality of actual dispositions of a projective imaging device: (i) moving the projecting imaging device to the each actual disposition, and (ii) acquiring a respective projective image of the body, using the projective imaging device at the each actual disposition; (b) based on the projective images, estimating the actual dispositions; and (c) based on the estimated dispositions, transforming the projective images into the output image volume.

According to the present invention there is provided an imaging system for acquiring an image volume of a body, including: (a) a projective imaging device for acquiring a plurality of projective images of at least a portion of the body at actual respective dispositions of the projective imaging device; and (b) a processor for estimating the actual dispositions from the projective images and for transforming the projective images into the image volume, the transforming being based on the estimated dispositions.

According to the present invention there is provided a method of navigating a probe in a body cavity of a patient, including the steps of: (a) acquiring a plurality of images of at least a portion of the body cavity, using an imaging device, while measuring, for each image, a respective disposition of the imaging device relative to a reference frame, each image being acquired at a different respective disposition; (b) selecting one of the first images to use as a guide image; and (c) displaying the guide image along with an icon representative of a disposition of the probe within the body cavity.

According to the present invention there is provided a method of treating a body of a patient, including the steps of: (a) simultaneously: (i) acquiring a first image of at least a portion of the body, using an imaging device, (ii) measuring a disposition of the imaging device relative to a reference frame, and (iii) measuring a disposition of the body relative to the reference frame; (b) restoring the imaging device and the body to respective dispositions that are equivalent to the measured dispositions; and (c) performing a medical procedure on the body with reference to the first image after the restoring of the imaging device and of the body to the equivalent dispositions.

According to the present invention there is provided a method of treating a body of a patient, including the steps of: (a) simultaneously: (i) acquiring a first image of at least a portion of the body, using an imaging device, (ii) measuring a disposition of the imaging device relative to a reference frame, and (iii) measuring a first disposition of the body relative to the reference frame; (b) measuring a second disposition of the body relative to the reference frame; and (c) performing a medical procedure on the body with reference to the first image and with reference to all three dispositions.

The patient upon whom the methods of the present invention are practiced could be either a person or an animal. The term "medical procedure" as used herein should be construed as including veterinary procedures.

The term "probe" as used herein should be construed as including any device or instrument, such as a catheter, an endoscope or a surgical tool, that is introduced to the body of a patient and that is navigated towards a target for the purpose of performing a medical procedure. The medical procedures that fall within the scope of the present invention include but are not limited to diagnostic procedures and therapeutic procedures, including surgical procedures.

According to a first aspect of the present invention, a plurality of projective images of at least a portion of a body cavity are acquired by a projective imaging device such as fluoroscope 22 at different respective dispositions relative to a reference frame, while measuring these dispositions, for example by using a disposing system. Each projective image includes a point that corresponds to a target point-of-interest in the body cavity; these points in the projective images are termed herein "projections" of the target point-of-interest. A location of the point-of-interest, relative to the reference frame, is estimated, preferably by picking the projections of the point-of-interest on two or more projective images, constructing rays corresponding to the picked projections, and computing the location, relative to the reference frame, of the point-of-nearest-mutual-approach of the rays. The projections may be picked manually. Alternatively, the projections are picked manually on a first projective image and automatically on subsequent projective images, for example by using standard image processing and feature recognition techniques to track the projection from image to image. Alternatively, the projective images are displayed successively and repeatedly, along with an icon that represents a point in space. The coordinates of the point are varied until the icon substantially coincides with all the projections. Alternatively, the projective images are transformed into an image volume, preferably by backprojection, and the target point-of-merest is picked directly in the image volume.

With the location of the target point-of-interest relative to the reference frame now known, a probe is inserted in the body cavity. The location of the probe is measured, preferably using a locating system, and the probe is moved towards the target point-of-interest.

Preferably, a contrast agent is introduced to the imaged portion of the body cavity prior to imaging.

Preferably, the location of at least one intermediate point-of-interest, relative to the reference frame, also is estimated from the projective images, and the probe is moved towards the target point of interest with reference to a display of icons that represent the estimated locations of the points-of-interest and the measured location of the probe. This display may be from any convenient point of view. In particular, this display may be from a point of view different from the points of view from which the projective images were acquired.

A system for implementing the first aspect of the present invention includes a projective imaging device for acquiring the projective images; a disposing system for measuring the disposition of the projective imaging device relative to the reference frame as the images are acquired; a mechanism for estimating the location of the point-of-interest relative to the reference frame, based on the acquired images; and a locating system for measuring the location of the probe in the reference frame.

Preferably, the disposing system includes a disposition implement associated with the projective imaging device and a disposing implement associated with the reference frame. Alternatively, the disposing system includes a disposing implement associated with the projective imaging device and a disposition implement associated with the reference frame. Preferably, the disposing system is an electromagnetic disposing system, a magnetic disposing system, an acoustic disposing system or a stereopair optical system.

Preferably, the locating system includes a location implement associated with the projective imaging device and a locating implement associated with the reference frame. Alternatively, the locating system includes a locating implement associated with the probe and a location implement associated with the reference frame. Preferably, the locating system is an electromagnetic locating system, a magnetic locating system or an acoustic locating system.

The accurate transformation of projective images into an image volume is addressed by a second aspect of the present invention, intended for use with a relatively mechanically unstable projective imaging device such as fluoroscope 22.

According to a first variant of the second aspect of the present invention, the projective images are transformed into the image volume, preferably by backprojection, according to respective nominal dispositions of the projective imaging device relative to a reference frame. To ensure that the projective imaging device really is in these nominal dispositions when the projective images are acquired, the actual dispositions of the projective imaging device are measured. If an actual disposition differs from the corresponding nominal disposition, the projective imaging device is moved until the actual disposition substantially coincides with the nominal disposition, and only then is the corresponding image acquired. The projective image device may be moved manually, or automatically via a feedback loop. The corresponding imaging system includes the projective imaging device, a disposing system for measuring the dispositions of the projective imaging device, a mechanism for moving the projective imaging device to make the actual dispositions coincide with the nominal dispositions, and a processor for transforming the projective images into the image volume.

According to a second variant of the second aspect of the present invention, the dispositions of the projective imaging device are measured explicitly as the projective images are acquired, and the acquired projective images are transformed into the image volume according to the measured dispositions, preferably by backprojection. The corresponding imaging system includes the projective imaging device, a disposing system for measuring the dispositions of the projective imaging device, and a processor for transforming the projective images into the image volume according to the measured dispositions of the protective imaging device.

Preferably, the disposing system, of the devices of the first and second variants of the second aspect of the present invention, includes a disposition implement associated with the projective imaging device and a disposing implement associated with the reference frame. Alternatively, this disposing system includes a disposing implement associated with the projective imaging device and a disposition implement associated with the reference frame. Preferably, this disposing system is an electromagnetic disposing system, a magnetic disposing system, an acoustic disposing system or a stereopair optical system.

According to a third variant of the second aspect of the present invention, the projective images are transformed into the image volume, preferably by backprojection, according to respective actual dispositions of the projective imaging device. Because these actual dispositions are not known initially with sufficient accuracy to effect the transformation, these actual dispositions are estimated from the projective images themselves, and the transformation then is based on the estimated dispositions. Preferably, the estimating of the actual dispositions is effected by transforming the projective images into a working image volume, on the assumption that the images were acquired at respective computational dispositions of the projective imaging device; and then correcting the computational dispositions, on the basis of the preliminary image volume, to obtain the estimated dispositions. Preferably, the correcting of the computational dispositions is effected by, for each computational disposition, computing a respective synthetic projective image from the working image volume; comparing the synthetic projective image to the corresponding acquired protective image; estimating, based on the comparison, the difference between the computational disposition and the actual disposition; and adjusting the computational disposition by subtracting this difference from the computational disposition. This transforming of the acquired projective images into the working image volume, and this correcting of the computational dispositions, are iterated until the estimated differences between the computational dispositions and the actual dispositions are negligible.

The imaging system of the third variant of the second aspect of the present invention includes the projective imaging device and a processor for performing the relevant calculations.

Preferably, in all three variants of the second aspect of the present invention, the projective imaging device is a fluoroscope.

According to a third aspect of the present invention, directed at navigating a probe within the body cavity of the patient, a plurality of first images of at least a portion of the body cavity is acquired at different respective dispositions of the imaging device relative to a reference frame, while measuring these dispositions. One of the first images is selected as a guide image, and the guide image is displayed along with an icon that represents the true disposition of the probe within the body cavity.

Preferably, the dispositions of the imaging device are measured using a disposing system that includes a disposition implement associated with the imaging device and a disposing system associated with the reference frame. Alternatively, the dispositions are measured using a disposing system that includes a disposing implement associated with the imaging device and a disposition implement associated with the reference frame. Preferably, the disposing system is an electromagnetic disposing system, a magnetic disposing system, an acoustic disposing system or a stereopair optical system.

Preferably, a contrast agent is introduced to the portion of the body that is to be imaged prior to acquiring the plurality of first images.

To facilitate the correct display of the icon, the disposition of the probe relative to the common reference frame also is measured. Preferably, the disposition of the probe is measured using a disposing system that includes a disposition implement associated with the probe and a disposing implement associated with the reference frame. Alternatively, the disposition of the probe is measured using a disposing system that includes a disposing implement associated with the probe and a disposition implement associated with the reference frame. Preferably, the disposing system is an electromagnetic disposing system, a magnetic disposing system or an acoustic disposing system.

Also according to the third aspect of the present invention, directed towards invasive medical procedures generally, a first image of at least a portion of the body of a patient is acquired while measuring both the disposition of the imaging device and the disposition of the patient relative to a common reference frame. Subsequently, both the body of the patient and the imaging device are restored to dispositions that are equivalent to the dispositions of the body of the patient and of the imaging device when the first image was acquired, and a medical procedure is performed on the body of the patent with reference to the first image. "Equivalent dispositions", as understood herein, means that the disposition of the body of the patient relative to the imaging device (or. equivalently, of the imaging device relative to the body of the patient) after restoration is the same as when the first image was acquired.

Preferably, the dispositions of the body of the patient and of the imaging device are measured using disposing systems that include respective disposition implements associated with the imaging device and with the body of the patient and a common disposing system associated with the reference frame. Alternatively, the dispositions are measured using disposing systems that include respective disposing implements associated with the imaging device and with the body of the patient and a common disposition implement associated with the reference frame. Preferably, the disposing systems are electromagnetic disposing systems, magnetic disposing systems, acoustic disposing systems or stereopair optical systems.

Preferably, a contrast agent is introduced to the portion of the body that is to be imaged prior to acquiring the first image.

Preferably, the medical procedure includes navigating a probe to a point-of-interest in the targeted portion of the patient's body, with reference to the first image.

Preferably, after the body of the patient and the imaging device are restored to their equivalent dispositions, a second image is acquired, and the medical procedure is performed with reference to both images. If the medical procedure includes navigating a probe to a point-of-interest in the targeted portion of the patient's body, then the disposition of the probe relative to the common reference frame also is measured. Preferably, the disposition of the probe is measured using a disposing system that includes a disposition implement associated with the probe and a disposing implement associated with the common reference frame. Alternatively, the disposition of the probe is measured using a disposing system that includes a disposing implement associated with the probe and a disposition implement associated with the common reference frame. Preferably, the disposing system is an electromagnetic disposing system, a magnetic disposing system or an acoustic disposing system.

Also according to the third aspect of the present invention, directed towards invasive medical procedures generally, a first image of at least a portion of the body of a patient is acquired while measuring both the disposition of the imaging device and the disposition of the patient relative to a common reference frame. Subsequently, the disposition of the patient is measured again, in case the patient has moved since the first disposition measurements, and a medical procedure is performed on the patient with reference to both the first image and all three measured dispositions.

Preferably, the dispositions of the body of the patient and of the imaging device are measured using disposing systems that include respective disposition implements associated with the imaging device and with the body of the patient and a common disposing system associated with the reference frame. Alternatively, the dispositions are measured using disposing systems that include respective disposing implements associated with the imaging device and with the body of the patient and a common disposition implement associated with the reference frame. Preferably, the disposing systems are electromagnetic disposing systems, magnetic disposing systems, acoustic disposing systems or stereopair optical systems.

Preferably, a contrast agent is introduced to the portion of the body that is to be imaged prior to acquiring the first image.

Preferably, the medical procedure includes navigating a probe to a point-of-interest in the targeted portion of the patient's body. This navigation includes measuring the disposition of the probe relative to the common reference frame. Preferably, the disposition of the probe is measured using a disposing system that includes a disposition implement associated with the probe and a disposing implement associated with the common reference frame. Alternatively, the disposition of the probe is measured using a disposing system that includes a disposing implement associated with the probe and a disposition implement associated with the common reference frame. Preferably, the disposing system is an electromagnetic disposing system, a magnetic disposing system or an acoustic disposing system.

Under the third aspect of the present invention, the imaging device may be either a protective imaging device or a representational imaging device, so that the first image may be either a projective image or a representational image. The preferred projective imaging device is a fluoroscope.

An important difference between prior art computer-aided surgery and the first and third aspects of the present invention should be noted. In prior art computer-aided surgery, if a 3D image volume is used to guide the navigation of a surgical tool within the patient, then this image volume is acquired prior to surgery. That guide image volume then must be registered to the frame of reference of the disposing system that is used to track the surgical tool. Because the locations of the intermediate points of interest of the first aspect of the present invention, as well as the guide image of the third aspect of the present invention, are acquired with the help of location and disposition systems that share a common component that is associated with a common reference frame, no such registration is necessary. For example, in FIG. 1A, the location system (under the first aspect of the present invention) or the disposition system (under the third aspect of the present invention) for catheter 26 includes transmitter 30 and receiver 32; the disposition system for fluoroscope 22 includes transmitter 30 and receiver 40; and the disposition system for the body of patient 24 includes transmitter 30 and receiver 38, with a common reference frame for all three receivers 32, 38 and 40 being defined by common transmitter 30.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of performing invasive medical procedures with the help of a single imaging device, particularly with the help of a single projective imaging device such as a fluoroscope. Specifically, the present invention can be used to facilitate intrabody navigation of a probe in a medical procedure such as stent deployment in a coronary artery.

The principles and operation of invasive medical procedures according to the present invention may be better understood with reference to the drawings and the accompanying description.

The present invention is explained herein with reference to stent deployment in a coronary artery as an example of an invasive medical procedure. This example is merely illustrative, and should not be construed as limiting the scope of the present invention, which is applicable to any invasive medical procedure that requires intra-body navigation of a probe to a point-of-interest.

Figure 1B:
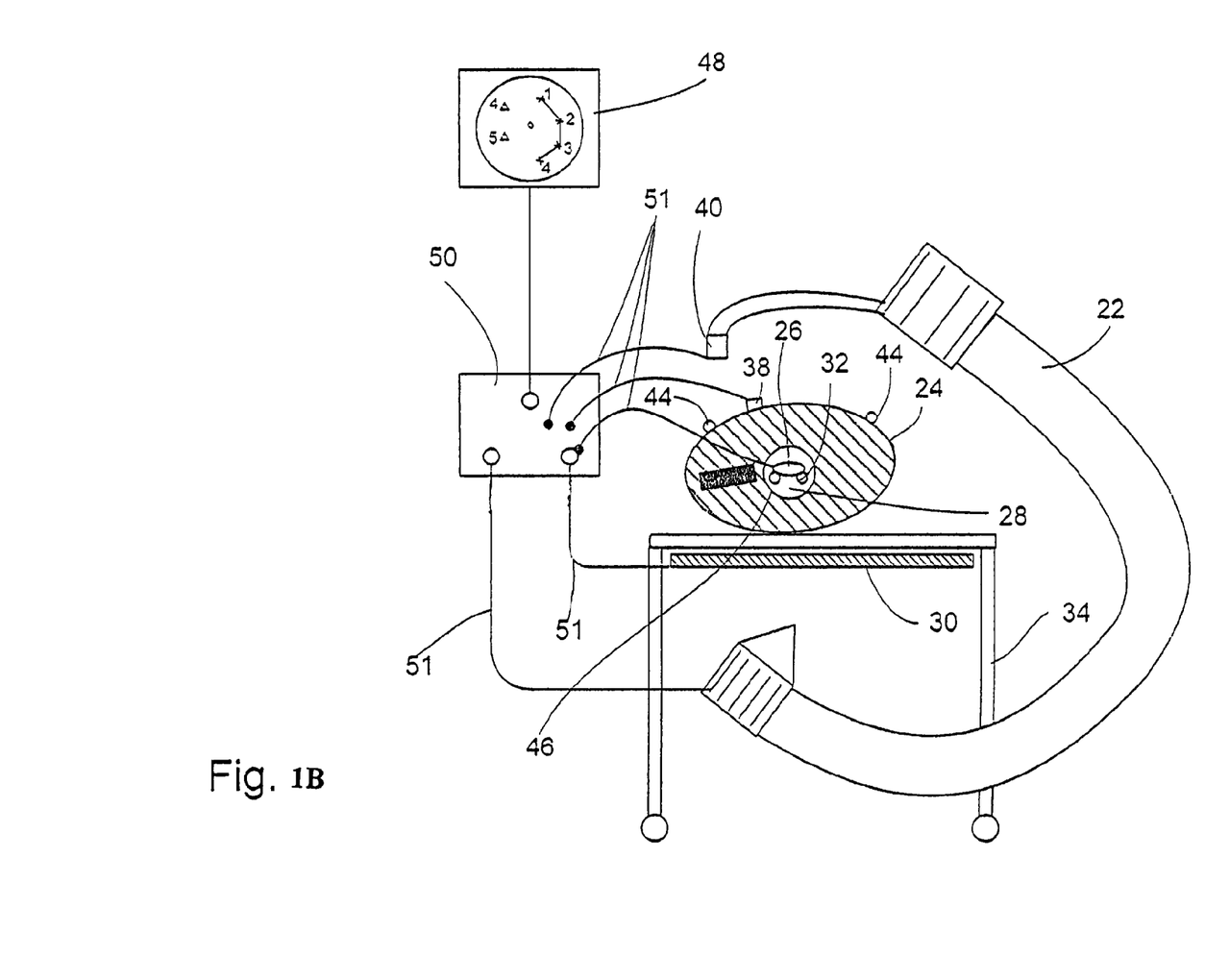
FIG. 1B shows the system of FIG. 1A modified according to the present invention by the removal of the representational imaging device, FIG. 2 (prior art) is a more detailed illustration of the C-mount fluoroscope of FIGS. 1A and 1B.

Referring again to the drawings, FIG. 1B, which is identical to FIG. 1A with representational imaging device 52 and receiver 40;* removed, illustrates a system of the present invention. In the context of the example of deployment of a stent in a coronary artery, body cavity 28 represents a coronary artery tree and catheter 26 is a catheter that is used to carry the stent to the blockage.

Figure 2:
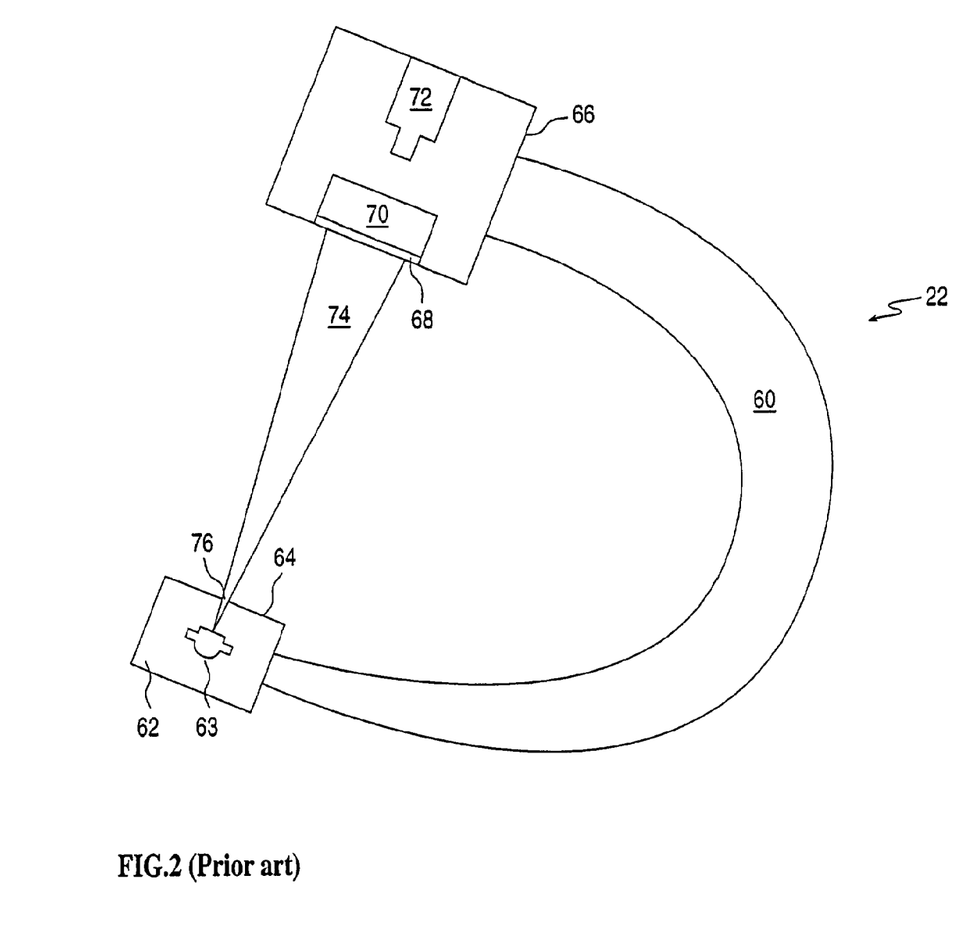

FIG. 2 illustrates C-mount fluoroscope 22 in more detail, in schematic cross-section. C-mount fluoroscope 22 is based on a C-arm 60. At one end of C-arm 60 is an X-ray source 62 that includes an X-ray tube 63 and a collimator 64. At the other end of C-arm 60 is an imaging tube 66 that includes an anti-scatter grid 68, an image intensifier 70 and a CCD camera 72. Collimator 64 blocks the X-rays emerging from X-ray tube 63 except at an aperture 76. A cone 74 of X-rays emerges from aperture 76 and impinges on anti-scatter grid 68 and imaging tube 70. The image thus created in imaging tube 70 is captured by camera 72. Depending on the spatial density distribution in an object such as patient 24 that is traversed by cone 74, each element of the CCD array of camera 72 receives more or less light from imaging tube 70, and the corresponding pixel of the protective image produced by fluoroscope 22 is correspondingly darker or lighter.

Each element of the CCD array receives X-rays in a very narrow subcone of cone 74, corresponding to how much of cone 74 is subtended by the portion of the image created in imaging tube 70 that is focused onto that element. The attenuation of this X-ray subcone is proportional to the integrated density of the material traversed by the subcone between X-ray tube 63 and imaging tube 66. Conceptually, this subcone can be treated as a geometric ray from X-ray tube 63 to imaging tube 66. Because the disposition of fluoroscope 22 is measured by computer 50 with the help of transmitter 30 and receiver 40, computer 50 knows the true location of X-ray tube 63 and every CCD element of camera 72 for every image acquired by fluoroscope 22. Therefore, for every pixel of an image acquired by fluoroscope 22, computer 50 can form a mathematical representation of the corresponding ray.

Figure 3:
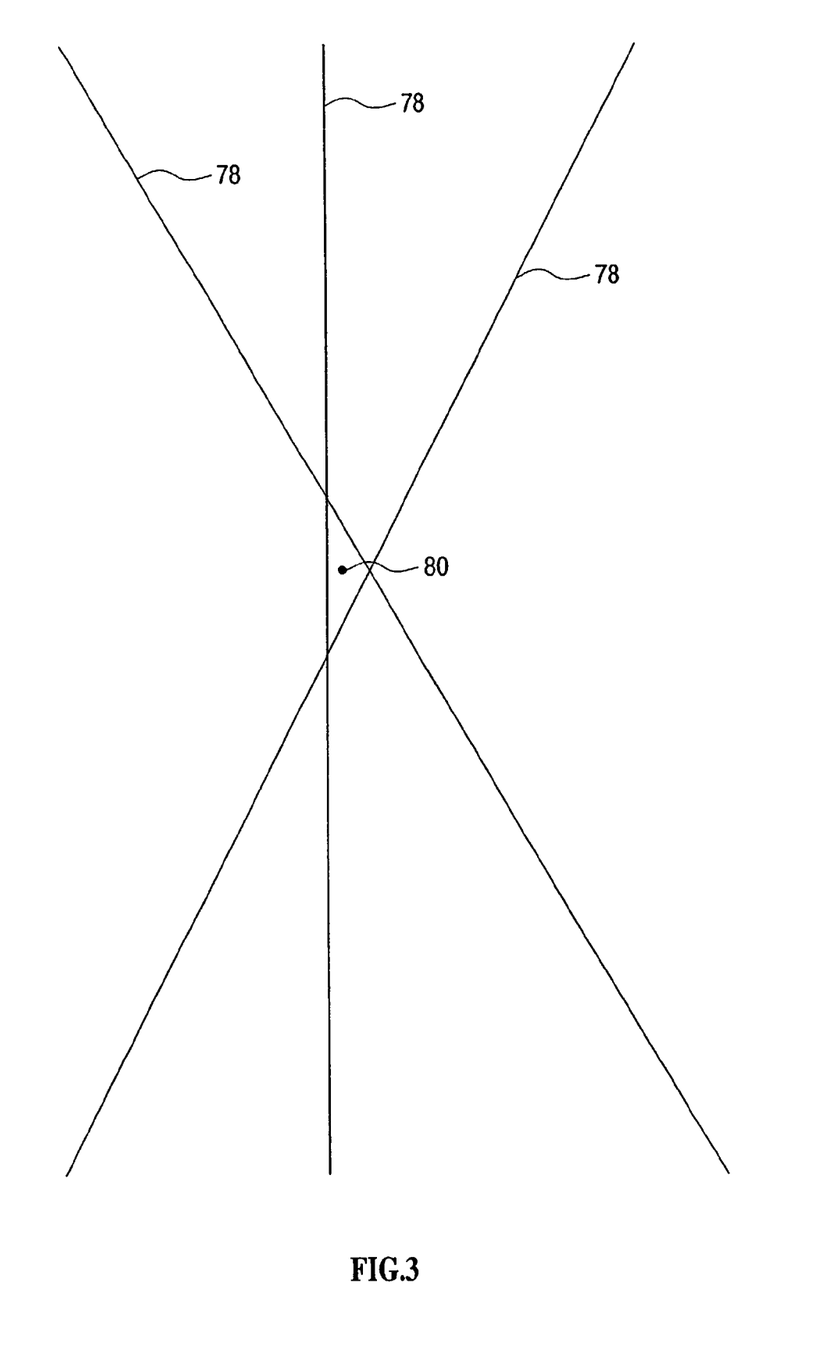
FIG. 3 illustrates the near intersection of three rays.

According to the first aspect of the present invention, as applied to the deployment of a stent in a coronary artery, a contrast agent is injected into coronary artery tree 28, and then several images of coronary artery tree 28 are acquired, using fluoroscope 22, from several angles. Projections of points of interest, such as the blockage to be opened by the stent, and such as branch points of coronary artery tree 28 that must be traversed on the way to the blockage, appear on these images. These projections are picked on these images as displayed on display unit 48. FIG. 3 shows, for three projections of one particular point-of-interest, three corresponding rays 78. In general, rays 78 do not intersect; but there is a point in space, labeled in FIG. 3 by reference numeral 80, such that the sum of the distances from point 80 to rays 78 is less than the sum of the distances from any other point to rays 78. Point 80 is referred to herein as the "point of nearest mutual approach" of rays 78. Given mathematical representations of rays 78, computer 50 computes the coordinates of point 80 in the reference frame of transmitter 30. These coordinates are an estimate of the true spatial location of the point-of-interest corresponding to rays 78.

A minimum of two rays 78 are required to define point 80. Therefore, at least two images of patient 24 must be acquired in order to estimate the locations of all the points-of-interest.

The projections of the points-of-interest may be picked manually. The preferred method of manual picking is to acquire a set of images at an evenly spaced series of dispositions of fluoroscope 22 and to display the images successively and repeatedly on display 48 as a movie. All the images are displayed in true mutual relative spatial location orientation, on the basis of the measured dispositions of fluoroscope 22 when the images were acquired. Along with the images is displayed an icon representing a point in space. Using an interactive input device such as a mouse or a trackball, the user changes the coordinates of the point represented by the icon until the icon coincides with the projection of the point-of-interest on each of the images. Note that when this has been accomplished, the coordinates of the point are approximately the true spatial coordinates of the point-of-interest, so that the coordinates of the point serve as an alternative to the point of nearest approach as an estimate of the true spatial location of the point-of-interest.

Alternatively, the projections of the points-of-interest are picked manually on the first acquired image and are tracked automatically to subsequent images. Standard image processing and feature recognition techniques are used to track the projections of each point-of-interest from image to image.

The true spatial locations of the points-of-interest having been established, the methods of WO 00/16684 are used to navigate the stent into position. Note that at this point in the procedure, it is no longer necessary to display any of the acquired images; nor is it necessary to acquire further images, with the attendant exposure of both the medical team and the patient to additional X-radiation, and with the attendant additional exposure of the patient to the contrast agent. Instead, only icons representing the locations of the points-of-interest are displayed on display unit 48, from any convenient point of view, along with an icon representative of the true location of catheter 26 relative to the points-of-interest, as determined using transmitter 30 and receiver 32 to measure the disposition of catheter 26.

Note further that the point of view from which the icons are displayed need not be, and generally is not, any of the points of view from which the images were acquired. In the present case of the points-of-interest being the branch points of coronary artery tree 28 and the target location in coronary artery tree 28, the set of points-of-interest contains all the information needed to navigate catheter 26 to the target location, and the images are redundant. In this context, the target location in coronary tree 28 is referred to herein as the "target point-of-interest" and the branches of coronary artery tree 28 are referred to herein as "intermediate point-of-interest". Nevertheless, if so desired, the points of interest may be displayed superposed on one of the images, from the point of view at which that image was acquired.

As an alternative to the projection picking and ray construction discussed above, the projective images acquired using fluoroscope 22 are transformed into an image volume, and the points-of-interest are picked in the image volume. How this transformation is accomplished, despite the relative mechanical instability of fluoroscope 22, is the subject of the second aspect of the present invention.

The mathematics of the tomographic transformation of a set of projective images into an image volume is well-established, being described, for example, in A. G. Ramm and A. I. Katsevich, *The Radon Transform and Local Tomography*, CRC Press, 1996; in F. Natterer, *The Mathematics of Computerized Tomography*, Wiley, 1989; in G. T. Herman et al., *Basic Methods of Tomography and Inverse Problems*, Hildger, 1987; and in G. T. Herman and Attila Kuba, *Discrete Tomography*, Birkhauser, 1999. All four of these publications are incorporated by reference for all purposes as if fully set forth herein. In particular, Ramm and Katsevich, on pages 276-302, discuss backprojection reconstruction in the case of a conical X-ray beam geometry such as X-ray cone 74.

Standard tomographic reconstruction algorithms assume that the input projective images are acquired at regularly spaced angles around the target being imaged, or equivalently, in the terminology used herein, at regularly spaced dispositions of the projective imaging device. The operator of fluoroscope 22 moves fluoroscope 22 (manually or under the control of computer 50) to successive nominal dispositions of fluoroscope 22, as indicated by the controls of fluoroscope 22. At each nominal disposition, the operator acquires a corresponding projective image. Because of inaccuracies in the construction of a typical fluoroscope 22, and because of the inherent mechanical flexibility of components of fluoroscope 22 such as C-arm 60, the actual disposition of fluoroscope 22 when each projective image is acquired usually is not quite identical to the corresponding nominal disposition of fluoroscope 22. The difference between the actual disposition of fluoroscope 22 and the corresponding nominal disposition of fluoroscope 22 is sufficient to introduce artifacts in the tomographically reconstructed image volume.

Figure 4:
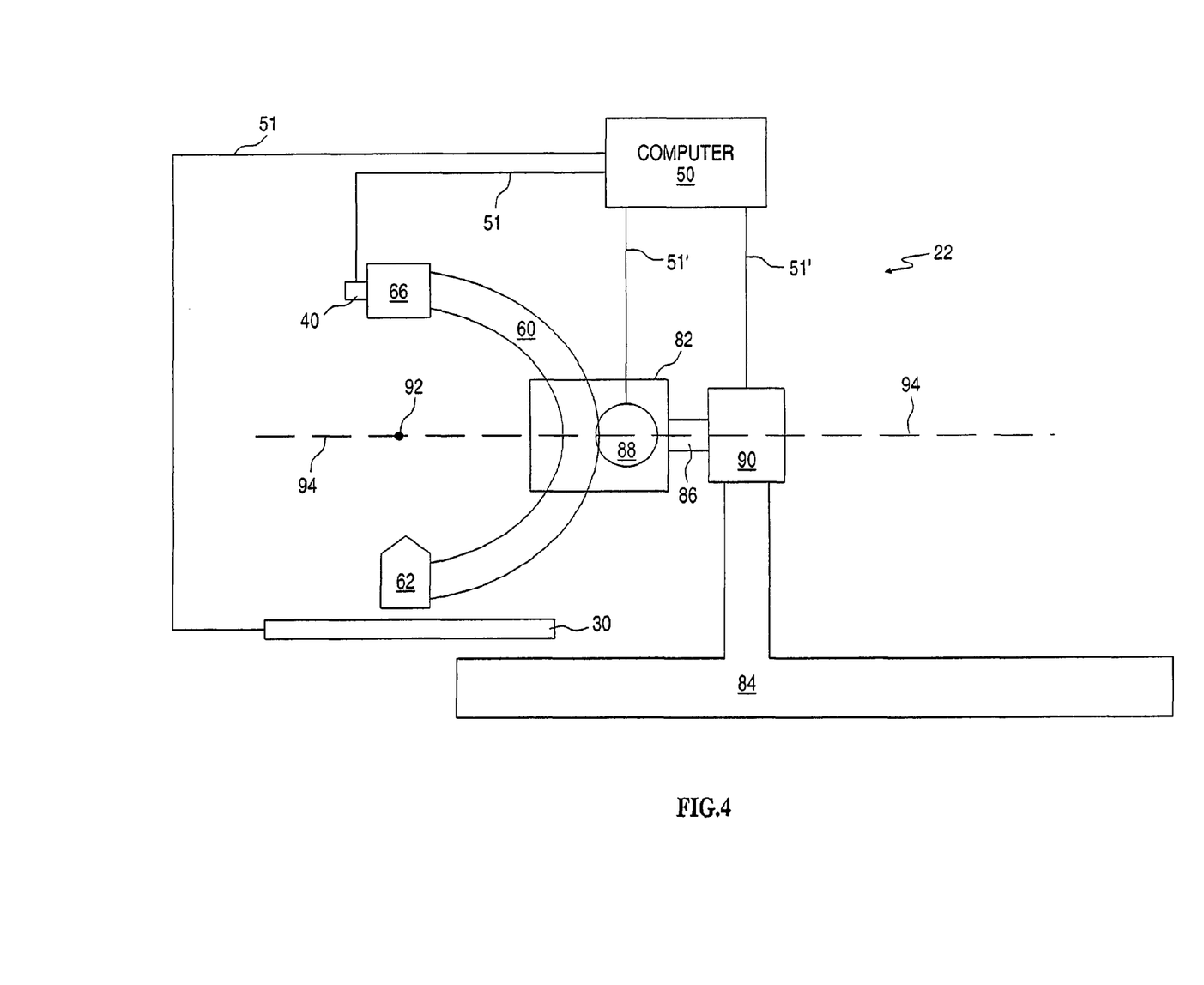
FIG. 4 shows further details of the mechanical construction of the fluoroscope of FIG. 1 as modified for the purposes of the present invention.

One way to overcome the mechanical instability of fluoroscope 22 is to ignore the indications of the nominal disposition of fluoroscope 22 as indicated by the controls of fluoroscope 22, but instead to use transmitter 30 and receiver 40 to measure the actual disposition of fluoroscope 22. Computer 50 computes this actual disposition from signals received from receiver 40 in response to electromagnetic radiation transmitted by transmitter 30. Computer 50 then displays this actual disposition on display unit 48. The operator then uses the controls of fluoroscope 22 to move fluoroscope 22 until the actual disposition displayed on display unit 48 is substantially identical to the desired nominal disposition. Alternatively, computer 50 itself moves fluoroscope 22 to the desired nominal disposition, as illustrated schematically in FIG. 4, which shows further aspects of the mechanical construction of fluoroscope 22 in (he context of other components of the system of the present invention as illustrated in FIG. 1B. As shown in FIG. 4, C-arm 60 is mounted in a yoke 82. A motor 88 in yoke 82 rotates C-arm 60 about an axis 92 that is perpendicular to the plane of FIG. 1. Yoke 82 itself is rigidly secured to a shaft 86 that is turned by a motor 90, so that motor 90 rotates yoke 82 about an axis 94 that is in the plane of FIG. 4. Motor 90 is secured to a base 84. Just as transmitter 30 and receiver 40 are connected to computer 50 by wires 51, so motors 88 and 90 are connected to computer 50 by wires 51'. As computer 50 receives signals from receiver 40 that are indicative of the actual disposition of fluoroscope 22, computer 50 computes the actual disposition of fluoroscope 22 and operates motors 88 and 90 to move C-arm 60 until the actual disposition of fluoroscope 22, as measured using transmitter 30 and receiver 40, is substantially the same as the desired nominal disposition. The cooperative action of computer 50, transmitter 30, receiver 40 and motors 88 and 90 constitutes a feedback loop for automatically moving fluoroscope 22 to the desired nominal disposition.

Figure 5:
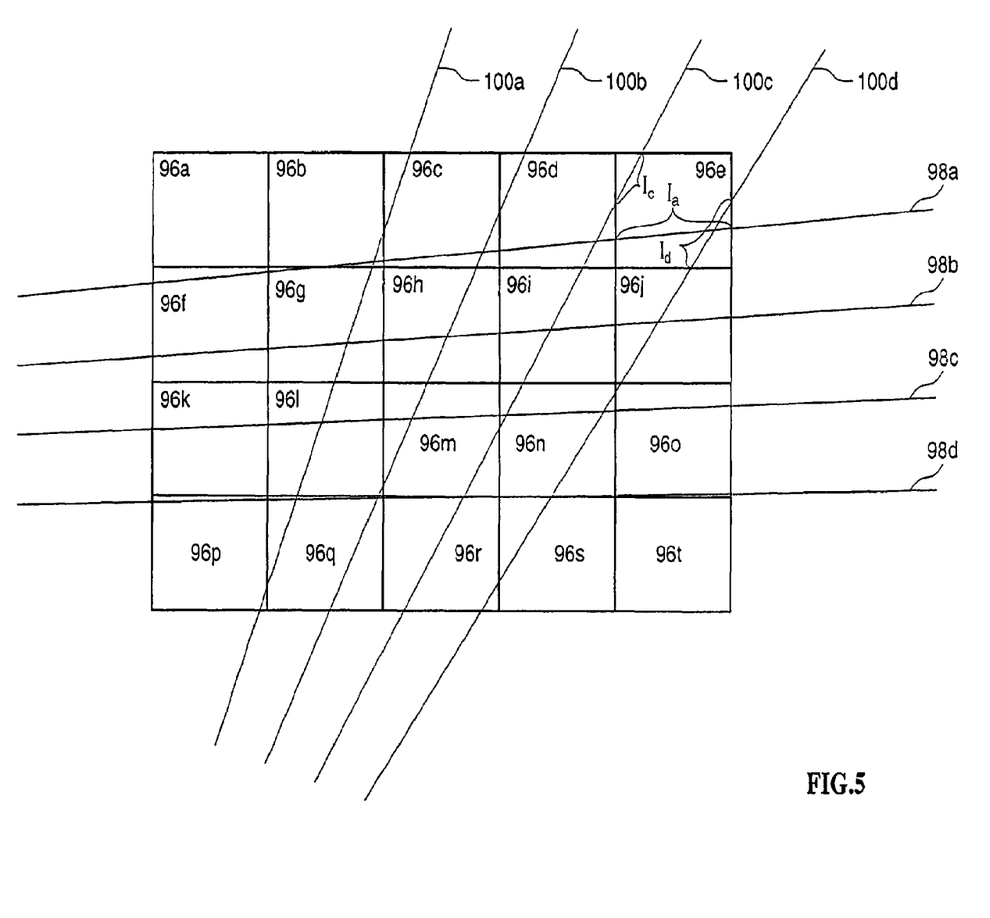
FIG. 5 illustrates the backprojection algorithm of the present invention.

A second way to overcome the mechanical instability of fluoroscope 22 is to move fluoroscope 22 to the nominal dispositions for acquiring the projective images, as indicated by the controls of fluoroscope 22; to measure the actual dispositions of fluoroscope 22 after fluoroscope 22 has been moved to these nominal dispositions; and to transform the acquired projective images into an image volume, not according to the nominal dispositions, but according to the actual dispositions. This transformation is done by a modified backprojection algorithm, as illustrated in FIG. 5. As noted above, for any disposition of fluoroscope 22, computer 50 can form, for each pixel of the projective image acquired at that disposition, a mathematical representations of the rays from X-ray tube 63 to the corresponding CCD element of camera 72. The space occupied by the imaged portion of the body of patient 24 is partitioned mathematically into a set of voxels. Some of these voxels are illustrated in FIG. 5 as squares 96, it being understood that this illustration is schematic, as voxels 96 actually are geometrically three-dimensional, and in fact typically are cubes. Also shown in FIG. 5 are some rays 98, corresponding to one disposition of fluoroscope 22, and some other rays 100, corresponding to another disposition of fluoroscope 22. In general, each voxel 96 is traversed by many such rays. The value assigned to each voxel 96 in the image volume is the sum of the pixels that correspond to the rays that traverse the voxel, weighted by the lengths of the portions of the rays that are inside the voxel. For example, if the value of the pixel associated with ray 98$a$ is $v_a$, if the value of the pixel associated with ray 100$c$ is $v_c$, and if the value associated with ray 100$d$ is $v_d$, then the value assigned to voxel 96$e$ is $I_a v_a + I_c v_c + I_d v_d$+corresponding terms for all the other rays that traverse voxel 96$e$.

Figure 6:
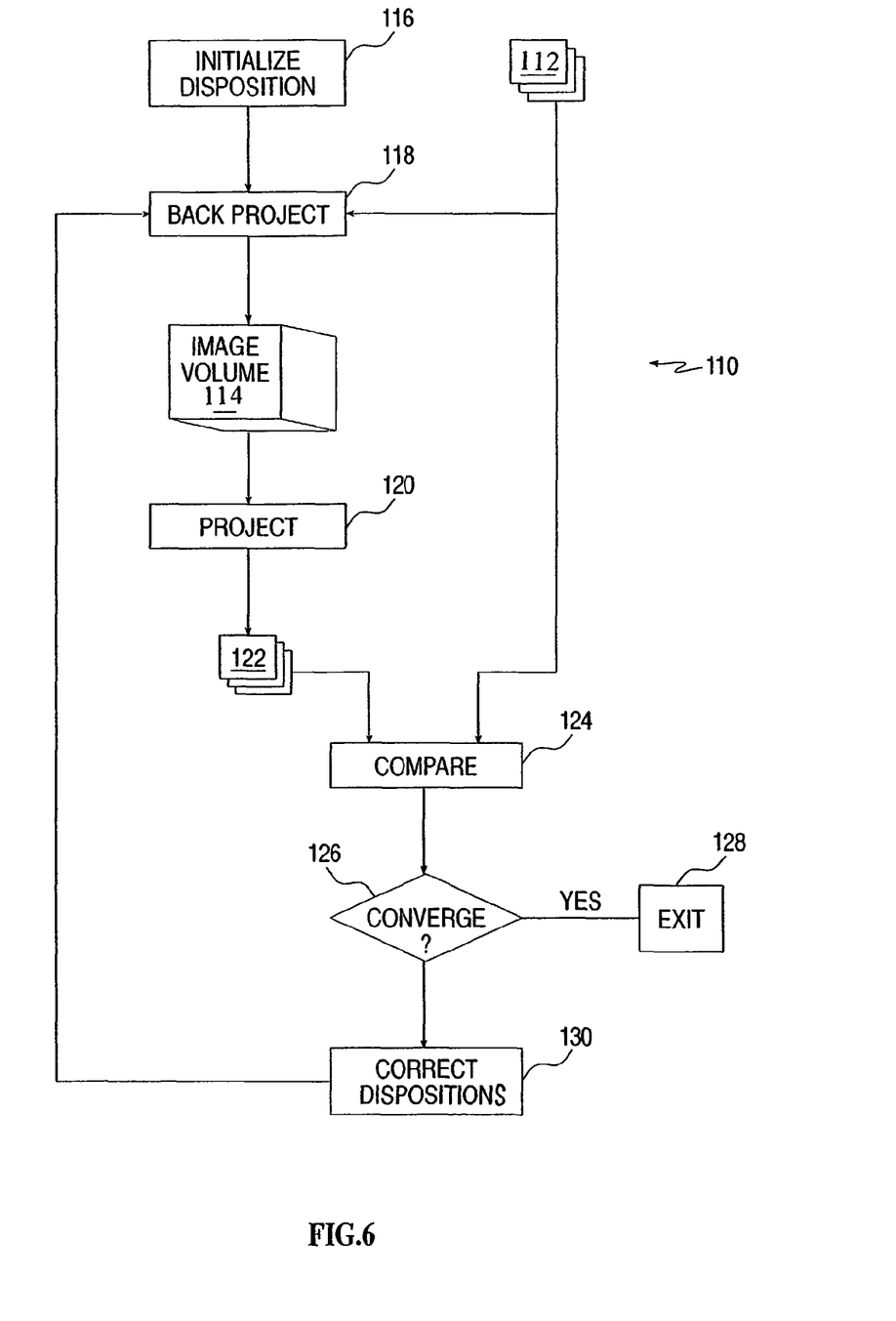
FIG. 6 is a flow chart for iteratively estimating actual dispositions at which the fluoroscope of FIG. 1 acquired a set of projective images while refining an image volume constructed from those projective images.

A third way to overcome the mechanical instability of fluoroscope 22 is to estimate the actual dispositions of fluoroscope 22 from the acquired projective images and to then transform the projective images into an image volume according to the estimated actual dispositions instead of according to the nominal dispositions. FIG. 6 shows a flow chart 110 of how this is accomplished. The input to flow chart 110 is a set 112 of acquired projective images and the corresponding nominal dispositions. The output of flow chart 110 is an image volume 114 that is initialized in flow chart 110 according to the nominal dispositions and then is corrected iteratively. In each iteration, acquired projective images 112 are backprojected into a working version of image volume 114 on the basis of the current estimate of the actual dispositions, corrections to these dispositions are computed from the working version of image volume 114 and from acquired projective images 112, and the corrections are applied to the current dispositions to obtain a new estimate of the dispositions to be used in the next iteration.

In more detail, in box 116, the computational dispositions to be used in the backprojection are initialized to the nominal dispositions. In box 118, acquired projective images 112 are backprojected according to the computational dispositions to obtain image volume 114. At this stage, image volume 114 is an approximate rendition of the image volume that would have been obtained if acquired projective images had been acquired at the computational dispositions. Therefore, in box 120, image volume 114 is projected forward according to these dispositions to obtain a set 122 of synthetic projective images, which are approximations of what acquired projective images 112 would have been if acquired projective images 112 had been acquired at the computational dispositions. In box 124, synthetic projective images 122 are compared to acquired protective images 112 to obtain estimates of the differences between the computational dispositions and the actual dispositions. For example, if a particular synthetic projective image is rotated relative to the corresponding acquired projective image, the degree of rotation is an indication of how much the corresponding computational disposition is rotated relative to the corresponding actual disposition. In box 126, these differences are compared to a threshold. If the differences are sufficiently small, the current version of image volume 114 is accepted as the final image volume (box 128). Otherwise, the differences are subtracted from the computational dispositions in box 130 and steps 118, 120, 124 and 126 are repeated.

According to the third aspect of the present invention, as applied to the deployment of a stent in a coronary artery, a contrast agent is injected into the target coronary artery tree 28, and then several images of coronary artery tree 28 are acquired, using fluoroscope 22, from several angles. The best of these images to use as a road map, for subsequent navigation of catheter 26 that bears the stent to the target location in coronary artery tree 28, is selected. This image is referred to herein as the "guide image". As each image is acquired, the corresponding disposition of fluoroscope 22 is measured using transmitter 30 and receiver 40, and the corresponding disposition of patient 24 is measured using transmitter 30 and receiver 38. There are two ways to navigate catheter 26 with reference to the guide image.

The first way to navigate catheter 26 is to restore fluoroscope 22 to the disposition of fluoroscope 22 at which the guide image was acquired. New images of coronary artery tree 28 are acquired using fluoroscope 22 while catheter 26 is inserted into coronary artery tree 28. The projection of catheter 26 appears on the newly acquired images as a shadow. The guide image is superposed on each newly acquired image, so that the instantaneous location of catheter 26 in coronary artery tree 28 can be seen. Catheter 26 is directed accordingly towards the target location in coronary artery tree 28.

The second way to navigate catheter 26 is to measure the disposition of catheter 26, using transmitter 30 and receiver 32," to display the guide image on display unit 48, and to display an icon, on display unit 48, that represents the shadow of catheter 26 that would ha—e been projected onto the guide image if the guide image had been acquired with catheter 26 at the measured disposition of catheter 26. Navigation of catheter 26 with reference to the guide image then is conducted similarly to navigation of catheter 26 with reference to both the guide image and the newly acquired images according to the first way of navigating catheter 26.

The first way of navigating catheter 26 minimizes the exposure of patient 24 to the contrast agent. The second way of navigating catheter 26 also minimizes the exposure of patient 24 and the operators of fluoroscope 22 to X-radiation.

The discussion, to this point, of the third aspect of the present invention, has assumed that patient 24 does not move between the acquisition of the guide image and the navigation of catheter 26. If patient 24 move, then the new disposition of the body of patient 24, relative to the reference frame defined by transmitter 30, must be measured, using transmitter 30 and receiver 38, and the navigation of catheter 26 must take into account the change in the disposition of the body of patient 24.

Under the first way of navigating catheter 26, fluoroscope 22 is moved until the relative dispositions of fluoroscope 22 and the body of patient 24 are the same as these dispositions were when the guide image was acquired. Let $D_f^1$ represent the disposition of fluoroscope 22, relative to the reference frame defined by transmitter 30, when the guide image was acquired. Let $D_b^1$ represent the disposition of the body of patient 24, relative to the reference frame defined by transmitter 30, when the guide image was acquired. Let $D_b^2$ represent the present disposition of the body of patient 24, relative to the reference frame defined by transmitter 30. $D_b^1$ and $D_b^2$ are related by a translation T and a rigid rotation R:

$$D_b^2 = RTD_b^1$$

Fluoroscope 22 must be moved to a corresponding new disposition $D_f^2$, relative to the reference frame defined by transmitter 30:

$$D_f^2 = RTD_f^1$$

Note that dispositions $D_f^1$ and $D_f^2$ are measured using transmitter 30 and receiver 40, and that dispositions $D_b^1$ and $D_b^2$ are measured using transmitter 30 and receiver 38.

Under the second way of navigating catheter 26, the icon that represents catheter 26, on the display on display unit 48, must be positioned in that display as though the guide image had been acquired with fluoroscope 22 at disposition $D_f^2$ instead of at disposition $D_f^1$.

As discussed above in the context of the first aspect of the present invention, once all the points-of-incrust have been acquired, a display of these points-of-interest on display unit 48 may be substituted for the guide image. This has the advantage of allowing navigation of catheter 26 with reference to a display oriented according to whatever point of view is most convenient. Of course, if so desired, the display may be from the point of view from—which the guide image was acquired, and the points-of-interest may be superposed on the guide image.

During the acquisition of the points-of-interest, the disposition of the body of patient 21 is measured using transmitter 30 and receiver 38. If patient 24 moves between the acquisition of the points-of-interest and the navigation of catheter 26, the disposition of the body of patient 24 is measured again, and the mathematical transformations described above are used to adjust the display of the icons to ensure that the icon representing catheter 26 still is displayed correctly relative to the icons representing the points-of-interest.

While the invention has been described with respect to a limited number of embodiments, it will be appreciated that many variations, modifications and other applications of the invention may be made.

What is claimed is:

1. A method of acquiring an output image volume of a body, comprising the steps of:
    (a) for each of a plurality of actual dispositions of a projective fluoroscopic imaging device:
        (i) moving said projective fluoroscopic imaging device to said each actual disposition;
        (ii) acquiring a respective projective image of the body, using said projective fluoroscopic imaging device at said each actual disposition;
    (b) based on said projective images, determining an estimated disposition for said each actual disposition; and
    (c) based on said estimated dispositions, transforming said projective images into the output image volume.

2. The method of claim 1, wherein said determining an estimated disposition for of said each actual disposition is effected by steps including:
    (i) transforming said projective images into a working image volume, said transforming assuming that each said acquired projective image was acquired at a respective computational disposition of said projective imaging device; and
    (ii) based on said working image volume, correcting said computational dispositions to obtain said estimated dispositions.

3. The method of claim 2, wherein said correcting is effected by steps including: for each said computational disposition:
    (a) computing a respective synthetic projective image of the body from said working image volume;
    (b) comparing said synthetic projective image to said respective acquired projective image;
    (c) estimating, according to said comparison, a difference between said computational disposition and said respective actual disposition; and
    (d) adjusting said computational disposition by subtracting said difference therefrom.

4. The method of claim 3, wherein said transforming of said projective images into said working image volume and said correcting of said computational dispositions are iterated until said estimated differences between said computational dispositions and said actual dispositions are negligible.

5. The method of claim 1, wherein said transforming is effected by backprojection.

6. The method of claim 1, wherein said projective imaging device is a fluoroscope.

7. The method of claim 1, wherein said estimating is based only on said projective images.

* * * * *